United States Patent
Tabani et al.

(10) Patent No.: US 6,945,257 B2
(45) Date of Patent: Sep. 20, 2005

(54) METHOD FOR CLEANING HOLLOW TUBING AND FIBERS

(75) Inventors: Yacoob Tabani, Basking Ridge, NJ (US); Mohamed Emam Labib, Princeton, NJ (US)

(73) Assignee: Princeton Trade & Technology, Princeton, NJ (US)

( * ) Notice: Subject to any disclaimer, the term of this patent is extended or adjusted under 35 U.S.C. 154(b) by 84 days.

(21) Appl. No.: 10/091,201

(22) Filed: Mar. 5, 2002

(65) Prior Publication Data

US 2002/0112743 A1 Aug. 22, 2002

Related U.S. Application Data

(63) Continuation-in-part of application No. 09/466,714, filed on Dec. 17, 1999, now Pat. No. 6,454,871, which is a continuation-in-part of application No. 08/880,662, filed on Jun. 23, 1997, now Pat. No. 6,027,572.

(51) Int. Cl.[7] .......................... B08B 9/00; B08B 9/027
(52) U.S. Cl. ............... 134/22.1; 134/22.11; 134/22.12; 134/22.18; 422/28
(58) Field of Search ............................ 134/22.1, 22.11, 134/22.12, 22.14, 22.18, 22.19; 422/28

(56) References Cited

U.S. PATENT DOCUMENTS

| | | | |
|---|---|---|---|
| 4,400,220 A | 8/1983 | Cole, Jr. ..................... 134/18 |
| 4,622,140 A | * 11/1986 | Lee et al. ................... 210/177 |
| 4,707,335 A | * 11/1987 | Fentress et al. .............. 422/44 |
| 4,767,539 A | 8/1988 | Ford ........................ 210/636 |
| 4,881,563 A | 11/1989 | Christian |
| 4,902,352 A | 2/1990 | Christian |
| 5,415,191 A | 5/1995 | Mashino et al. .......... 134/102.1 |
| 5,628,959 A | * 5/1997 | Kross ......................... 422/37 |
| 5,651,893 A | 7/1997 | Kenley et al. ............. 210/636 |
| 5,658,466 A | * 8/1997 | Kawaguchi et al. ........ 210/748 |
| 5,941,257 A | 8/1999 | Gruszczynski ............ 134/22.11 |
| 5,944,997 A | 8/1999 | Pedersen et al. ............ 210/636 |
| 6,027,572 A | 2/2000 | Labib et al. .................... 134/8 |
| 6,192,900 B1 | 2/2001 | Arnal et al. ................ 134/22.1 |
| 6,193,890 B1 | 2/2001 | Pedersen et al. ............ 210/636 |
| 6,423,152 B1 | 7/2002 | Landaas ...................... 134/10 |
| 6,454,871 B1 | 9/2002 | Labib et al. .................... 134/8 |
| 2002/0112743 A1 | 8/2002 | Tabani et al. |
| 2002/0189647 A1 | 12/2002 | Labib et al. |

FOREIGN PATENT DOCUMENTS

| | | | |
|---|---|---|---|
| EP | 490117 A1 | 12/1990 | ............ B08B/9/06 |
| EP | 213157 B1 | 10/1992 | ........... B01D/61/00 |
| EP | 160014 B1 | 1/1993 | ........... B01D/61/00 |
| EP | 634229 B1 | 7/1993 | ............ B08B/9/06 |
| EP | 289523 B1 | 1/1995 | ........... B01D/65/02 |
| GE | 893595 | 10/1953 | |
| SU | 1042826 A | 2/1981 | ............ B08B/9/02 |
| WO | WO 85/01449 | 4/1985 | ........... B01D/13/00 |
| WO | WO 86/05116 | 9/1986 | ........... B01D/13/00 |
| WO | WO 88/00494 | 1/1988 | ........... B01D/13/00 |

OTHER PUBLICATIONS

Azzopardi, B., "Drops in annular two–phase flow," *Int. J. Multiphase Flow*, vol. 23, Suppl., pp. 1–53 (1997).

(Continued)

*Primary Examiner*—Michael Barr
*Assistant Examiner*—Saeed Chaudhry
(74) *Attorney, Agent, or Firm*—Merchant & Gould P.C.

(57) ABSTRACT

Hollow porous fibers containing adhered contaminants are cleaned to remove the contaminants by backflushing a liquid to fill the pores, and adding a flow of gas so as to form a two-phase mixture of gas and bubbles of liquid that can scrub the fibers, loosening the contaminants and allowing them to be flushed from the hollow fibers. The method is particularly useful for cleaning hemodialyzers used for dialysis and hollow fiber modules used in water treatment and separations. The two phase flow method is specifically effective in cleaning piping systems having high length to diameter (l/d) ratios.

69 Claims, 4 Drawing Sheets

OTHER PUBLICATIONS

Barajas, A. et al., "The effects of contact angle on two–phase flow in capillary tubes,", *Int. J. Multiphase Flow*, vol. 19, No. 2, pp. 337–346 (1993).

Henstock, W. et al., "The Interfacial Drag and the Height of the Wall Layer in Annular Flow,", *AIChE Journal*, vol. 22, No. 6, pp. 990–999 (Nov. 1976).

Hewitt, G. et al., "Annular Two–Phase Flow,", *Pergamon Press*, pp. v–vii, 1–20, chapters 1–2 (Date unknown).

Klauer, J., "Piping: An examination of pipe self cleaning in high–purity water systems," *Ultrapure Water*, pp. 56–60 (Mar. 2001).

Reinemann, D., "Dairy operators guide to milking machine cleaning and sanitation,", *Paper written for presentation at the NRAES the Milking Systems and Parlors Conference*, 8 pages (Jan. 30, 2001).

Riedewald, F., "Biofilms in Pharmaceutical Waters," *Pharmaceutical Engineering*, 8 pages (Nov./Dec. 1997).

Tragardh, C., "Cleaning in air–water–flow," *Division of Food Engineering, Lund Engineering, Alnarp (Sweden)*, pp. 424–429 (Date unknown).

Triplett K., et al., "Gas liquid two–phase flow in microchannels. Part 1: two–phase flow patterns", *International Journal of Multiphase Flow*, vol. 25, pp. 377–380, 387–393 (1999).

Woodmansee, D. et al., "Mechanism for the removal of droplets from a liquid surface by a parallel air flow," *Chemical Engineering Science*, vol. 24, pp. 299–307 (1969).

* cited by examiner

METHOD FOR CLEANING HOLLOW TUBING AND FIBERS

This invention is a continuation-in-part of application Ser. No. 09/466,714 filed Dec. 17, 1999, now U.S. Pat. No. 6,454,871 which is a continuation-in-part of Ser. No. 08/880,662 filed Jun. 23, 1997, now U.S. Pat. No. 6,027,572.

This invention relates to a method for removing biofilm, debris, contaminants and the like from the surfaces of hollow passageways, including passageways which have irregular or complex shapes, or whose walls are permeable, using a water-based cleaning mixture.

BACKGROUND OF THE INVENTION

Interior surfaces of passageways, particularly small-bore or capillary tubing, as well as larger diameter pipes, ducts and the like, which may carry liquids, gases, or slurries, are very difficult to clean and to maintain in a clean condition. When the flow path is long and narrow, and more specifically when the length to diameter (l/d) is large, it is difficult to clean the surfaces by conventional liquid phase flushing, because such a long, narrow passageways limit liquid flow velocities by creating a high resistance to flow.

High l/d better describes the intended dimensions of the passageway. As examples, endoscope internal tubing has an l/d of about 500–2000; hemodialyzer hollow fibers have an l/d of about 1000–1500; dental chair tubing has an l/d of about 2000–3000; tubular membranes have an l/d of about 500–1500; piping systems, such as used for dairy, food and painting facilities, have an l/d in the range of 1000–3000; water systems and the like have an l/d of about 500–1500. Tubing diameters that can be cleaned according to the present method are from about 0.2 mm to about 10 cm or more, as long as a sufficient gas supply is made available.

As a result of such high l/d and other geometrical limitations, particularly in the case of small diameter tubing, shear stresses that could aid in the removal of contaminants from such tubing surfaces are limited. Low flow velocities also limit the usefulness of aqueous liquid cleaning solutions and solvents for the same reasons.

Cleaning of small diameter passageways is also difficult because of the nature, adhesion characteristics and solubility of certain types of residues. Fluid passageways which supply water, even purified water, develop bacterial and fungal growth from the water on their interior surfaces, as is well known. Bacteria present in the fluid strongly adhere to tubing surfaces and then grow laterally, forming what is known as biofilm, which an possess an adhesive strength of up to 120 Pascal. Biofilm is apparent to the touch as a slimy film and is composed of both organic residues and the multiplying microorganisms. The bacteria deposit on underlying structural matrices comprising polysaccharides with some peptide moieties, calcium carbonate and other materials which adhere to the surfaces of the passageways. This biofilm must be periodically removed because biofilm is the main cause of high bacterial counts and high levels of endotoxins.

In other situations, when an organic layer strongly adheres to the surface of pipes, tubing or other passageways, similar challenges are presented with respect to removal as in the biofilm case. Examples include organic materials deposited in dairy, food, and beverage equipment, and in the biopharmaceutical industries where the composition of debris in not biofilm.

However, removing biofilm, particles and other undesirable substances from capillary size fluid passageways is quite difficult. The biofilm is strongly adherent to passageway surfaces, whether the surfaces be of natural or synthetic materials. Treatment with chemical agents such as disinfectant and biocidal agents can kill the exposed surface bacteria and so reduce the contribution of the biofilm to the total bacterial count. However, the biofilm matrix structure remains an ideal host for new bacteria to colonize and grow. Thus these treatments are only partially and temporarily effective, and the original levels of bacteria return rapidly, sometimes within hours.

Cleaning of instruments by spraying with water or cleaning solutions is also well known. The spray may be generated by an aerosol can or an atomizing device, but it does not ensure complete cleaning of adherent debris either. Complete cleaning only occurs when the adhesion of the debris is overcome, as by shear stress.

In addition to biofilm, passageways of various medical devices may contain particles of various body tissues, mucous, unclotted or clotted blood or blood components, pathogens, macromolecules, proteins and the like, which are referred to hereinafter as "debris". It is necessary to remove this debris from the passageways in which it exists.

Hemodialyzers and hemofilters used in kidney dialysis are made of bundles of hollow fibers whose walls are permeable membranes, most commonly having a geometry which is of a tubular shape. They are difficult to clean.

Blood components including proteins, glycoproteins, carbohydrates, cells, platelets and the like are known to adhere to the surfaces of dialyzer materials, including fiber lumens, pore surfaces and resin materials present under the cap of the dialyzer. The adhesive strength of such blood components to dialyzer surfaces is high, and cannot normally be removed with conventional exposure to liquids alone. The difficulty of removing these substances from the dialyzer depends on the chemistry of the reagents used for dialyzer cleaning.

Acid reagents, such as peracetic acid, citric acid or phosphoric acid cause denaturing of blood proteins and make them adhere strongly to dialyzer surfaces. At the same time, these reagents increase the adhesive strength of other blood components. For example dialyzers cleaned or re-processed multiple times with a commercial cleaning solution lose over 50% of their water permeability due to the denaturing of proteins and other blood substances within the pore structure. Further, blood clots accumulate in the dialyzer over several cleaning cycles. Blood clots under the cap regions of a dialyzer are changed to solid, gritty substances that are almost impossible to remove, even with manual scrubbing.

Hemodialyzers, hemofilters and filters used in blood processing or oxygenation in common use comprise about 15,000 hollow fibers enclosed in a housing. Each hollow fiber is about 150–200 microns in the internal lumen diameter. On the dialysate side, a sodium bicarbonate solution is used that flows along the outside of the fibers. Blood flows to the inside of the fibers, exchanging solutes with the dialysate side and removing excess liquids and undesirable materials from blood through a thin membrane layer covering the lumen of the fibers. While low molecular weight solutes such as urea and creatinine, and some middle sized proteins, are removed, the loss of important blood proteins, such as albumin, is prevented. The effectiveness of this process is a function of the available membrane surface area that permits blood-dialysate solute exchange; it is estimated by the total cell volume (TCV), i.e., the volume of liquid that fills the available fibers. A typical TCV is about 110–120 ml for adults, and a blood cleaning dialysis treatment is delivered in about three hours. A patient uses a dialyzer, which is cleaned after each session, until it fails, or when the TCV is reduced to less than 80% of its value when new.

At present a hemodialyzer is sterilized with a liquid sterilant such as peracetic acid, formaldehyde, glutaraldehyde and the like, and stored for at least 13 hours. Because it is difficult to maintain a high TCV level and retain the pore size distribution in a re-used dialyzer at about the same level as a new one, only about 10–15 re-processings, and often fewer, can be carried out prior to failure, when the dialyzer must be discarded.

Blood clots that form inside the hollow fibers clog some of them, reducing the TCV; also blood clots form particularly in regions under the cap of the dialyzer. Protein layers also form on the lumen of hollow fibers which can hamper the removal of undesirable solutes from the patient's blood to the dialysate or liquid side. Precipitation of proteins and other molecules within the pore structure also clog the pores. Thus reprocessing or cleaning of the dialyzers is very important but has not been sufficiently addressed. Instead, up till now, the emphasis has been on preventing microbial infections by sterilization of the used dialyzers, while ignoring the clearance of undesirable solutes during dialysis treatment.

The most commonly used reprocessing solution is a peracetic acid sterilant available as Renalin®, a peracetic acid-hydrogen peroxide mixture available from the Minntech Corporation of Minneapolis, Minn. However, this solution, although it sterilizes the hemodialyzer, does not clean the pores by removing proteins, blood clots and the like, and does not clean under the cap regions adequately, where blood clots and other material tends to aggregate. Thus the dialyzers become fouled, limiting their number of re-uses, compromising dialysis treatment of patients, and raising the cost of dialysis because new dialyzers must be provided more frequently.

Another method in common use to reprocess hemodialyzers uses 0.5–1.0% hypochlorite bleach for cleaning. This is generally done by backflushing the bleach solution by pressurizing the dialysate compartment for a short time, followed by rinsing with water and filling the dialyzer, either with formaldehyde or glutaraldehyde sterilants. Although in principle this method should clean the pores, it is not effective to remove blood clots from the fiber lumen or from the under the cap regions of the dialyzer. Although this method is more effective in removing protein residues from the dialyzer, the number of times a dialyzer can be reprocessed is about the same as using the Renalin® method. Further, bleach increases the pore size and effects a shift in the pore size distribution in the membrane layer, leading to high loss of albumin in patients. This has been found to be the main cause of albumin loss in hemodialysis patients, which has an adverse effect on their health.

In response, the industry has re-formulated the composition of the membrane layer and introduced two types of polysulfone-based hemodialyzers—one for use with bleach reprocessing, and the other for use with peracetic acid. However, despite some improvements in dialyzer materials, albumin loss in patients remains a major issue with respect to the number of possible re-uses. Further, the bleach solution method is not efficient in maintaining the TCV above the 80% level of that of a new dialyzer, and maintaining the dialyzer in good functional condition for many re-uses.

Another recent cleaning method is based on citric acid, followed by preserving the dialyzers at high temperature to ensure disinfection. However, due to the low pH of citric acid solutions, protein layers deposited on the lumen surface of hollow fibers precipitate inside the pore structure of the membrane layer and are not removed by this processing method. The method does not adequately clean, and the prolonged elevated temperatures of disinfection leads to shell fatigue. Thus inadequate cleaning and the cost of energy to sterilize the dialyzer are major drawbacks to this method.

Still another method for reprocessing is by circulating hot water on a continuous basis between dialysis sessions. Again, only visible blood is removed. Maintaining the dialyzer at elevated temperatures denatures proteins in the blood, which remain in the lumen and pore structure, impairing clearance of middle solutes such as $\beta_2$-microglobulin (hereinafter beta-2M) during dialysis.

The clearance of beta-2M from patient blood during dialysis takes place by two mechanisms, ultrafiltration and adsorption onyo the surface of pore structures. Existing dialyzer reprocessing methods cannot achieve the desired clearance of beta-2M and other undesirable molecules because of the loww of pore volume due to precipitated proteins in the pore structure and by masking the polymer surface of the dialyzer fibers with a protein layer, that diminishes removal of such molecules by adsorption. The present method does achieve the removal of protein pore structure and of all surfaces, thus increasing the coefficient of ultrafiltration and the capacity of adsorption.

Another major limitation in existing reprocessing methods lies in their inability to equally clean both venous and arterial sides of the dialyzers. This differential fouling problem is caused by the fact that the dialyzer is mounted in one direction during dialysis treatment. Since the dialysate is pumped in the reverse direction to blood flow from the arterial side, a low pressure between the dialysate and blood compartments always exists at the venous side of the dialyzer. This results in more severe fouling of the hollow fiber lumen and pore structure on the venous side. None of the current reprocessing methods addresses this major problem.

In summary, none of the present cleaning methods can remove blood clots from hollow fibers and from under the cap areas of a dialyzer; remove accumulated protein deposits formed on the surface of the fiber lumen; remove protein and other biological materials from the pore structure of the dialyser; perform equivalent cleaning of the arterial and the venous sides of the dialyser; keep the dialyzer in such condition that it can effectively remove middle solutes such as beta-2M; nor increase the number of reuses while delivering optimum performance of the dialyzers, thereby achieving the best dialysis treatment of patients without compromise.

Another objectionable feature of present-day dialyzer cleaning, is the potential exposure of dialyzer reprocessing workers to infection and other consequences, since the cleaning operation often involves opening the dialyzer caps to manually remove blood clots from under the cap.

The present methods do not clean the dialyzer of protein deposits or other residues, and thus are deficient in that the required treatment function is not delivered to the patient, and the costs of treatment are increased.

Other suggestions for cleaning have been made, but they have proven to be no more effective in cleaning, and some have other problems as well.

Thus a method of cleaning and sterilizing dialyzers, including fiber lumen, pore structure, under the cap regions and fouling on both the arterial and venous sides, and of increasing the number of reuses, bringing the properties of the dialyzer close to a new one, would be highly desirable.

SUMMARY OF THE INVENTION

We have found a method of cleaning and sterilizing hollow fiber membrane modules such as hemodialyzers, hemofilters and piping systems with high length to width ratio. The lumen, the membrane, the pore structure and the surface of the membranes and piping interiors are cleaned by pressurizing a cleaning agent of a preferred composition to infiltrate the cleaning solution into the lumen of the fibers, while injecting a gas at high velocity into the blood-lumen side so that a two phase flow, of a known liquid to gas ratio, is formed inside the hollow fibers or tubing. This combination of backflushing and two-phase flow loosens materials that have deposited on the lumen and in the pores of the hollow fibers, so that they can be readily flushed away.

In some types of dialyzers and hollow fiber modules, a premixed two phase flow having a known liquid to gas ratio is passed into the fiber lumen to remove protein deposits, blood clots and debris from the dialyzer or membrane module. The formation and delivery of this two phase flow depends on the membrane type, module geometry and characteristics of the piping system to be cleaned. Biofilm and debris can be readily removed from pipe interiors using this same method.

The present invention provides methods, compositions and devices for cleaning and sterilizing hemodialyzers that overcome existing inadequacies. The present method can clean all parts of a dialyzer, including fiber lumen, pore structure, and under the cap regions, and addresses the differential fouling of the dialyzer in the venous and arterial sides. The present method delivers both cleaning and sterilization of the dialyzer, increases significantly the number of re-uses, up to forty or more times. The present method also clears middle solutes, such as beta-2M, while minimizing the loss of albumin in patients over a large number of re-uses. Thus used dialyzers cleaned by the method and compositions of this invention approximate a new one in being able to deliver a like-new dialysis dose for each re-use. Cleaning of piping systems having a high l/d according to this invention achieves superior results compared to liquid flushing with considerable saving in reagents and cleaning times.

DETAILED DESCRIPTION OF THE INVENTION

The present invention uses two phase flow to clean and sterilize used dialyzers, using particular cleaning compositions, at particular fluid dynamic regimes, and provides means of delivery to the dialyzers. The cleaning solution is most effective when the pH of the solution is over 7, i.e., at least slightly alkaline; and most effectively, is over about 11.3. Most particularly, the cleaning solution of the invention should have a pH higher than the isoelectric point of blood proteins, which is about 11.1. Strong electrostatic repulsion is favored, since dialyzer surfaces and precipitated proteins become negatively charged, and have a high surface potential. The addition of a chelating agent to an alkaline cleaning solution further enhances cleaning, since it sequesters multivalent ions associated with proteins.

In dialysis, contaminants present in the blood, such as small particles of any undesirable substances including macromolecules, adsorbed serum proteins, blood cells, cell fragments, platelets, salts and other soluble or dispersed blood constituents, must be removed. This is done as described above by passing a dialysate into a dialyzer which removes undesirable molecules from blood. The dialyzers comprise a housing containing up to thousands of hollow, permeable membrane fibers and appropriate inlets and outlets for blood and dialysate fluid. Permeable membranes are more difficult to clean than solid surfaces, because impurities that are meant to be removed can lodge either at the membrane's exposed surface, or within the membrane pore structure, the surfaces within the membrane pore structure being the most difficult to clean.

At present, hemodialyzers can be re-used up to about 30 times. However, for some patients, who may represent roughly one-quarter of hemodialysis patients, hemodialyzers clog more quickly, and thus can only be re-used three or four times. A better method of cleaning and disinfecting hemodialyzers between uses could extend their useful life, with consequent economic savings, and possibly improve the biological performance of re-used hemodialyzers. Even if the improved cleaning only extended the life of those hemodialyzers which are presently re-used three or four times, by up to 15 times, the economic savings would be considerable.

Membrane filters, at present, are cleaned with harsh liquid phase chemicals and/or large quantities of hot water, including backflushing. Even though such membranes are cleaned at regular intervals, they never return to their original flux and clearance efficiency levels. Essentially, this means a permanent de-rating of the membrane's capacity.

Better cleaning methods for passageways would be useful to more completely and easily remove the biofilm, debris, contaminants and the like. In any filtration application, an improved cleaning method would either extend the membrane service life or improve its performance.

The present major forms of sterilization for hollow fibers are heat, harsh chemicals and radiation. Sometimes these methods cannot be used. Methods which stay close to ambient conditions, use a benign chemistry, use a small volume of a cleaning solution, and are simple to perform would be an improvement. Thus a cleaning method that can be carried out rapidly, effectively and inexpensively, that does not employ extreme temperatures, harsh or toxic chemicals or radiation, or use a large volume of cleaning liquids, would be highly desirable.

The membranes to be cleaned according to the invention comprise hollow fibers or hollow tubes having a membrane layer on the inside of the hollow fiber which may perform microfiltration, ultrafiltration, nanofiltration or reverse osmosis. The bundle of fibers is generally encased in a housing for the purpose of performing filtration, dialysis or dia-filtration. The fibers may also be immersed in a liquid rather than in a housing.

In one embodiment of the invention, a hemodialyzer used in dialysis treatment is cleaned by simultaneously pressurizing a cleaning agent in the dialysate side to infiltrate a known amount of the cleaning agent into the lumen of fibers, while injecting a known amount of gas at high velocity into the blood/lumen side of the dialyzer so that a two-phase flow with a minimum range of liquid to gas ratios that will flush the membrane pores and remove solid materials and molecules from all surfaces of the dialyzer are formed in situ inside the hollow fibers.

Figure 1:
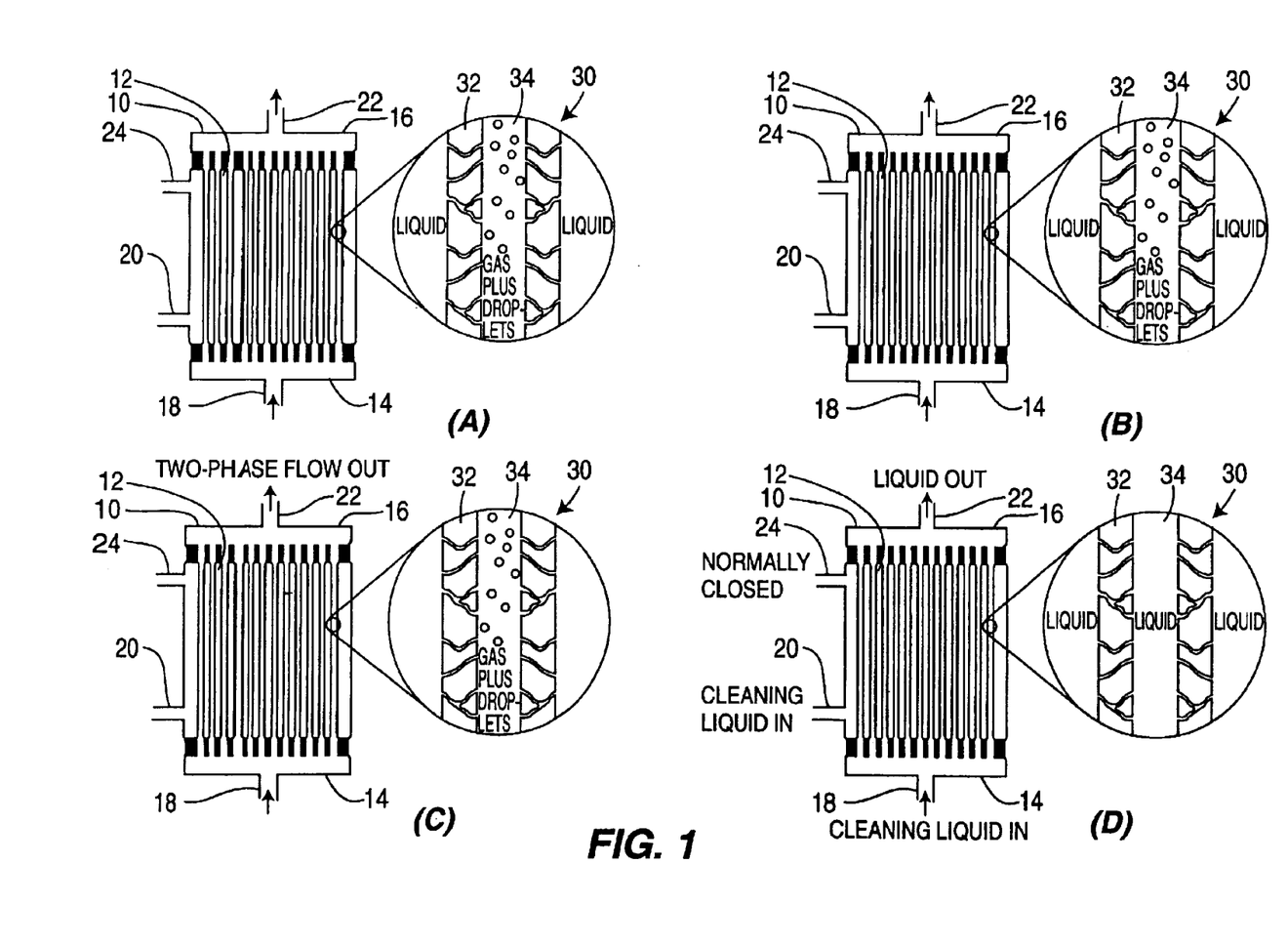
FIGS. 1A, 1B, 1C and 1D illustrate four methods used to clean hemodialyzers according to this invention.

This dialyzer is shown in FIG. 1A. A housing 10 enclosing a plurality of hollow fiber membranes 12 includes two cap regions 14 and 16. An inlet tube 18 allows a flow of air to enter the blood side end cap 14, and a liquid inlet 20 allows a flow of cleaning solution into the dialysate side of the housing 10. An exit tube 22 allows the mixed phase flow of solution and air to exit the dialyzer through the end cap 16. Another tube 24 on the dialysate side is normally closed.

An expanded view of a single fiber is shown at 30. Each fiber is made of a porous membrane layer 32 and a hollow tube 34. In use, liquid flows along the fiber and through the interstices of the porous membrane 32 into the hollow tube 34 of the fiber, and out the exit tube 22.

The cleaning agent must be able to effect cleaning of the pores of the membrane layer located on the lumen side of the hollow fibers. The gas used to make the two phase flow mixture is applied at high velocity in the range of 10–500 feet/sec. The velocity of the gas must be sufficient to form droplets of the liquid in the gas stream, and sufficient to effect instability at the surface of the fiber boundary layer, so as to force solid materials out of the hollow fiber. A suitable droplet size is about 20 microns and higher, preferably from 50–250 microns in diameter. Thus blood clots and deposited or adsorbed protein are effectively removed from the lumen of the hollow fibers.

The liquid to gas ratio of this in-situ two phase mixture is between 1:50 and 1:6000. The droplet size of the liquid dispersed in air is between 50–250 microns in diameter, depending on the gas velocity and the surface tension of the liquid. The high turbulence and the localized shear stress conditions caused by this two phase flow are sufficient to remove blood clots, protein deposits and other blood residues from beneath the cap regions 14 and 16. The high velocity mixture's swirls, eddies and vortices, formed inside of the under-cap regions, achieve high cleaning efficiency. If the present cleaning method is used after each dialysis session, no cumulative effect of blood clots or adsorbed proteins occurs in the cap regions, as can be seen by visual inspection through the housing. Thus the dialyzer is kept at optimal functionality.

The two-phase flow can be continuous, or can be pulsed by closing off the air periodically. When the flow of air is shut off, the cleaning agent from the pressurized dialysate side fills all or portions of the fibers, and this liquid is then pushed out of the fiber lumens to the under cap regions and exits the dialyzer through the cap 22, when the air flow is resumed. This manipulation of the two phase flow can be important in dislodging blood clots from inside the fiber lumen and from the under the cap regions. The on-off air flow timing and the shape of the pulse used depend on the type of dialyzer to be cleaned, and its specifications.

When the cleaning solution is pressurized on the dialysate side and mixed with air introduced from the blood side, a unique method for cleaning hollow fibers is created. The mixed phase flow pushes blood clots and deposited proteins from the hollow fibers, as long as one side of the fiber is accessible to the flow. The cleaning solution from the dialysate side weakens the adhesive strength of blood clots and deposited proteins present in the lumen of the fibers, and renders them removable by the shear stress generated by the two phase flow. Localized shear stress created by this two phase flow as the liquid droplets sweep the lumen of fibers is about two to three orders of magnitude higher as compared to the bulk shear stress generated by a single phase liquid flow alone. The liquid to gas ratio that allows the creation of this localized shear is necessary to achieve effective cleaning. The range of liquid to gas ratio can be between 1:50 to 1:6000.

By reversing the direction of flow, or backflushing, and by application of a pulsed flow, the cleaning effectiveness of the two-phase flow of the invention is further enhanced. Flow reversal provides access for liquid to enter the fiber from either direction and subjects the surface of the fibers to a sweeping action to ensure effective cleaning of the dialyzer, including the end cap regions.

An effective liquid to gas ratio can also be attained by applying a continuous air stream in the lumen side of the dialyzer while supplying cleaning liquid from the dialysate side by controlling the flow rate of the liquid. This can also achieve a liquid to gas ratio range between 1:50 to 1:6000 and the high velocities required for effective cleaning of the pore structure and end caps, and to remove blood clots from different parts of the dialyzer.

In another embodiment of the present invention, part of the liquid needed for two phase flow is introduced by pressurizing a cleaning agent from the dialysate side, while the remaining portion of the liquid is introduced with gas from the blood side, see FIG. 1B. The final liquid to gas ratio is maintained in the same range of 1:50 to 1:6000, as described above.

The two liquids may be the same or different; if different, exposure of the pore structure or the fiber lumen can be restricted to a particular liquid composition. For example, a hypochlorite bleach solution, introduced to the dialyzer by pressurizing the dialysate compartment, can cause an increase in the pore size of the hollow fibers, which leads to albumin loss in patients undergoing hemodialysis treatment. When the bleach solution is not infiltrated through the membrane pore structure from the dialysate side, and is used only in the lumen side, the negative effects of bleach can be minimized. Thus two liquids can be used for cleaning the dialyzer, one introduced from the dialysate side to clean the pores, and the other introduced as a two phase mixture from the lumen or blood side to clean the lumen and under cap regions. This is shown in FIG. 1B.

A third method of the invention is to introduce the two phase flow as a premixed gas-liquid mixture through the lumen or blood side, see FIG. 1C. The fiber lumens are cleaned of blood clots and proteins, as are the under-cap regions. To clean both the venous and arterial sides, the direction of flow is reversed. This method is useful when the membrane layer has very small pores, such as those used to perform nanofiltration and reverse osmosis processes or, in the case of low flux hemodialyzers. Thus when backflushing does not allow infiltration of sufficient liquid to form the requisite two phase flow mixture, such as membranes with low ultrafiltration coefficients, e.g., narrow size ultra filters, nano filters, and filters used for reverse osmosis, this method can be used. The same method is particularly effective for cleaning piping systems with high l/d.

Still another embodiment of the invention employs two distinct liquid compositions to clean hemodialyzers or hollow fiber membrane modules having similar geometries, see FIG. 1D. The dialysate or shell side is filled with a liquid cleaning agent and maintained under pressure, while another liquid cleaning agent is passed at high velocity inside the lumen, from the blood side in the case of hemodialyzers. The pressure difference between the two sides is adjusted to control the flow.

It is believed that the presence of a residual protein layer on the surface of dialyzers makes them more biocompatible, and prevent immune reactions, including complement activation factors and the like. Cleaning compositions having a high pH, e.g., pH of 11.3 to 11.9, without hypochlorite bleach, appears to satisfy this criterion. The recovery is not complete, but almost complete recovery of a dialyzer's water permeability and ultrafiltration coefficient ($K_{uf}$) are achieved with reprocessing without deterioration of the membrane material itself.

Figure 5:
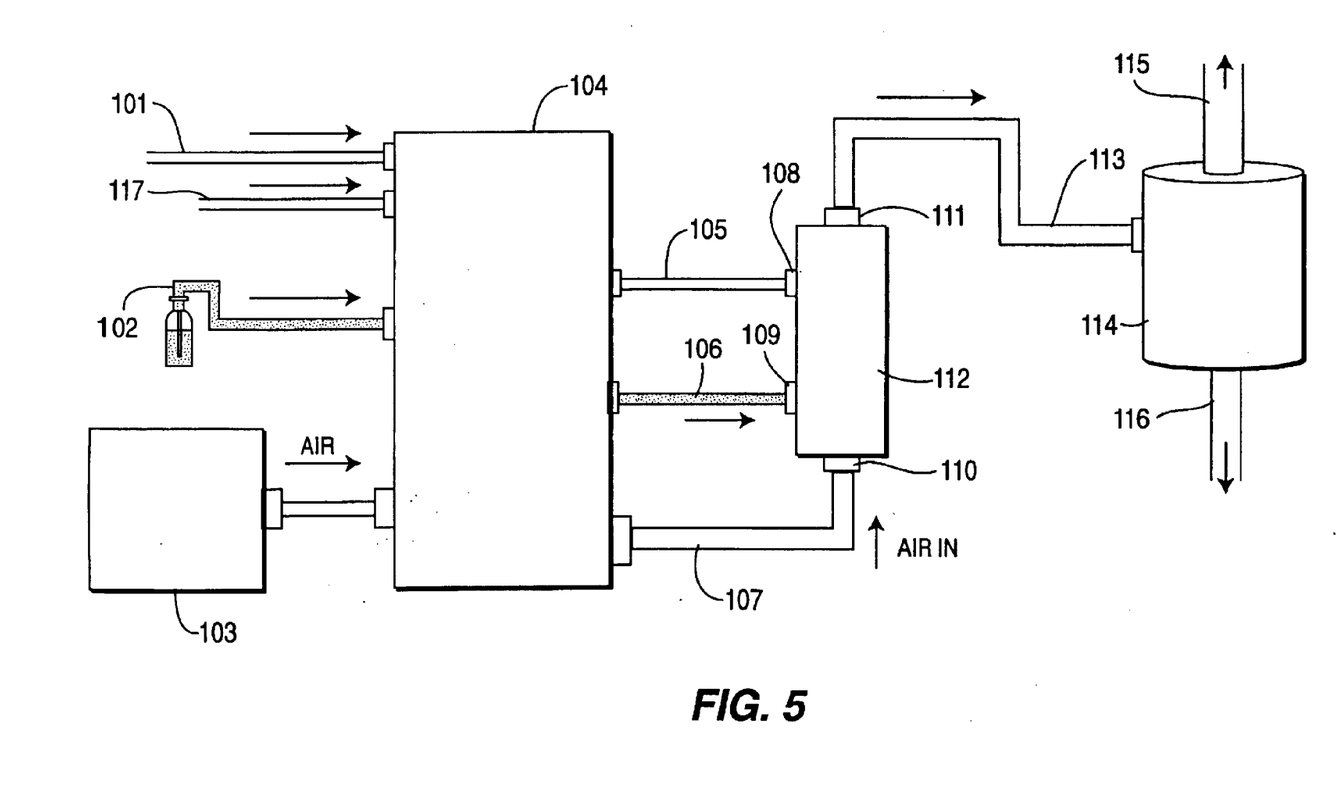
FIG. 5 is a schematic view of an illustrative reprocessing device for cleaning a dialyzer with a two phase cleaning system.

FIG. 5 illustrates a device for applying the two phase flow cleaning solution of the invention.

A two phase device 104 has an inlet 101 for clean water, and an inlet 102 for cleaning solution. An air compressor 103 passes compressed air into the device 104. The cleaning solution can pass into the dialyzer 112 through inlet 109, and compressed air can be fed to the dialyzer 112 from air inlet 107 through the lumen inlet 110. This mixture is passed out of the dialyzer through lumen outlet 111. The mixture is directed through tube 113 to a mist separator 114, where liquid and gas are separated. Air is exhausted through outlet 115 and liquid drains through outlet 116. The dialysate port 108 is normally closed.

During the rinsing step, water is supplied through line 101 and enters the dialyzer through the inlet port 109 and can be mixed with air through lumen inlet 110. The rinsing water exits from the lumen outlet 111. The dialyzer 112 is then filled with a liquid sterilant through line 117 using the device 104.

The dialyzer can be cleaned using a premixed two phase mixture in the device 104 to enter the dialyzer through inlet 110 and exiting through the outlet 111 to the mist separator 114. The cleaning solution can also be passed through the dialysate side by keeping the inlet 109 open. To re-process a dialyzer with liquid only, device 104 delivers liquid through the ports 106 and 110 to the dialyzer 112. The liquid exits through port 111.

Figure 6:
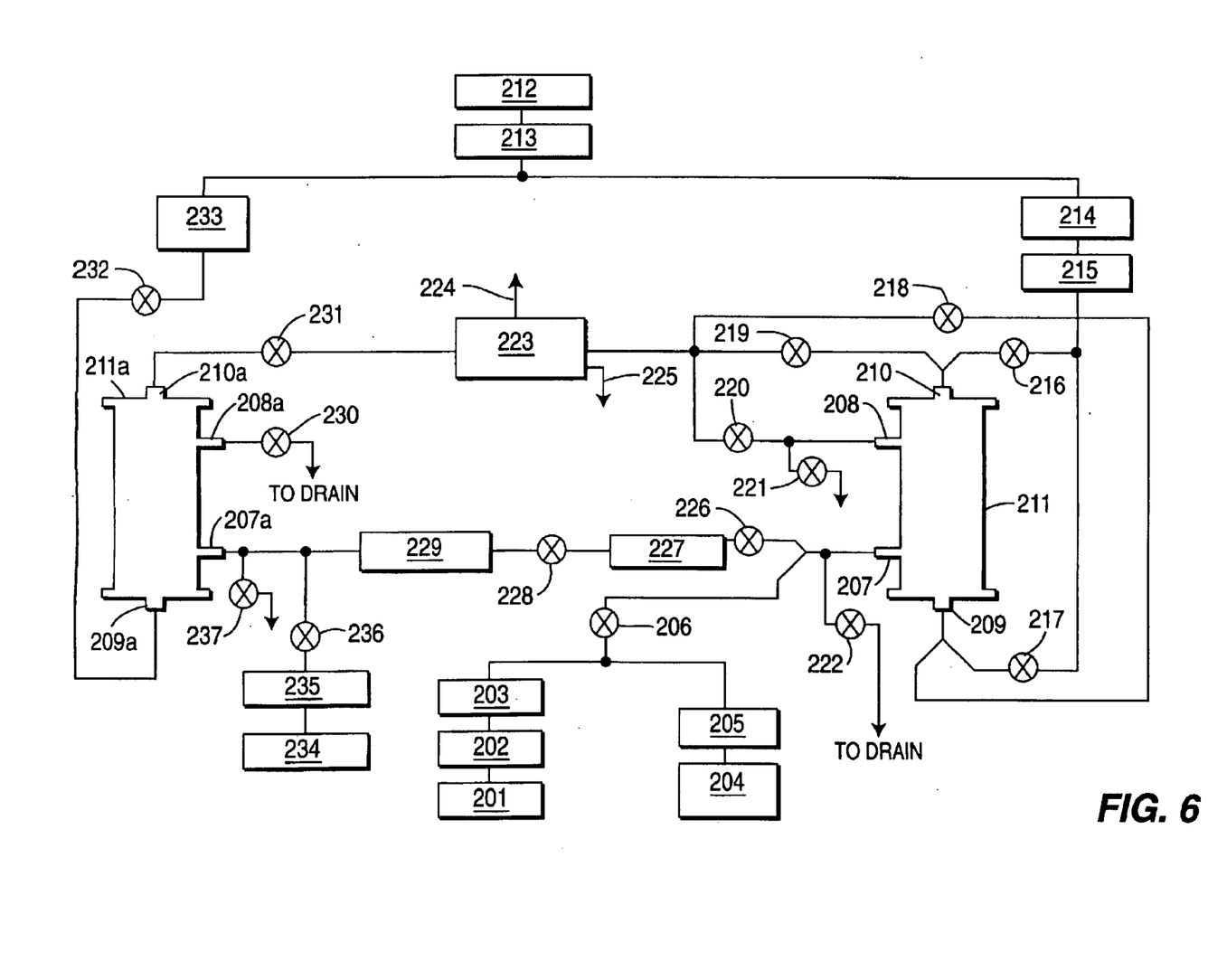
FIG. 6 is a more detailed schematic view of a reprocessing device for cleaning a dialyzer with a two phase cleaning system.

FIG. 6 is a more detailed schematic view of a two phase dialyzer re-processing device. A cleaning solution in tank 204 is passed using a pump 204 from a source 201 through a pump 202 and liquid heater 203 to the dialysate inlet port 207 through valve 206, where it is allowed to infiltrate through fiber lumens to the dialyzer 211. Two phase flow is formed from air supplied by a compressor 212 through a high efficiency air filter 213 regulated by a regulator 214 and heated with a heater 215. This solution enters the lumen inlet 209 through a valve 217 and mixes with the liquid in the fiber lumen that exits the dialyzer 211 through the lumen outlet 210. It is directed to a mist separator 223 through a valve 219, where the liquid and gas segregate; air exhausts through outlet 224 and liquid drains through outlet 225. When reversing the flow, air enters the dialyzer through port 210 with the valve 216 open, and mixes with the cleaning liquid in the fiber lumen to exit the dialyzer through port 209 when it is directed to the outlet port 208. This outlet port 208 is normally closed by means of a valve 220. During cleaning, flow reversal can be repeated several times. The cleaning agent is drained from the dialysate sides by opening valves 221 and 222.

At the end of the cleaning cycle, water is supplied through dialysate inlet port 207 through a valve 226 where it is mixed with air entering the lumen inlet 209. This rinsing water exits through the lumen outlet 210 and is directed to the mist separator 223.

The dialyzer can also be rinsed by passing water to the dialysate inlet 207a from water source 2271 through a valve 228 using a water heater 229. This rinse water may be mixed with air to enter the dialyzer through inlet port 229a through a pressure regulator 233 and a valve 232. The rinsing water exits the dialyzer 211a from the lumen exit 210a to the mist separator 223 through a valve 231. The port 208a is closed via valve 230. The dialyzer is then drained by opening the valves 230 and 237. At the end of the rinse cycle, the dialyzer 211a is filled with a liquid sterilant from a reservoir 234 using a pump 235 and a valve 236 to enter the dialysate inlet 207a, exiting through port 210a.

Cleaning compositions based on hypochlorite bleach, and used at high pH, appear to increase the water permeability of the dialyzer due to chemical degradation of the PVP components of the membrane materials, such as the polysulfone-based dialysers F80A made by the Fresenius Company. Adjustment of pH, bleach concentration, temperature and time of reprocessing produces acceptable recovery of dialyzer functions without adversely affecting membrane materials in the above polysulfone dialyzers. Other types of dialyzers tolerate cleaning compositions based on hypochlorite bleach without negatively affecting membrane materials, such as those made of polyamide, supplied by the Gambro Corporation, or cellulose-based dialyzers made by the Baxter Company. Thus some adjustments of cleaning composition may be required to apply the methods of this invention and are to be considered to be within the scope of the invention.

The invention will be further described in the following Examples and Controls. In the Controls and Examples, unless otherwise noted, reprocessing according to the invention uses the following sequence.

The cleaning solution was heated to 50° C. and pumped into the dialysate side of the hemodialyzer for two minutes. Filtered air was then supplied to the interior of the hollow fibers for five seconds, shut off for 5 seconds, allowing the liquid to fill all or part of the lumen of the hollow fibers. This sequence was repeated for 30 seconds, and the direction of air flow was reversed. The same on-off cycle was repeated in like manner. The air to liquid ratio was 200:1 and the set pressure of air was 35 psig. The flow rate of cleaning solution through the pump was 400–450 ml/min.

The hemodialyzer was then rinsed with water at room temperature for 10 minutes at a flow rate of about 500 ml/min. The TCV was then measured. A liquid sterilant is added to fill the dialyzer prior to re-use.

Control 1

A dialysis center responsible for treating 180 end stage renal disease (ESRD) patients used two conventional dialyzer reprocessing methods.

The first method was based on bleach-formaldehyde, and was used for several years. This method, A, involves a brief backflushing from the dialysate side at a concentration of 0.5 to 1.0% of bleach and a pH of about 9.0 at room temperature. The dialyzer was rinsed with pure water and filled with a formaldehyde liquid sterilant.

The second method, B, involves manually cleaning the dialyzer with pure water and filling it with Renalin® using a "Renatron"® machine made by Minntech Corporation of Minneapolis, Minn., and was followed for at least two years.

Figure 2:
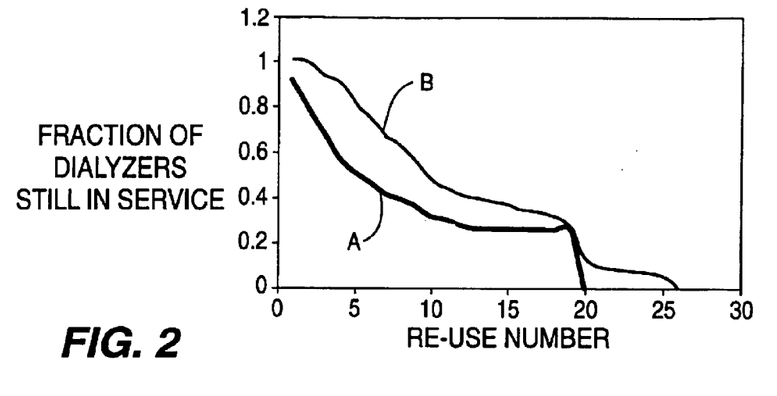
FIG. 2 is a graph comparing the number of re-uses for dialyzers cleaned using two known methods.

About 1000 dialyzers processed with the above two methods were analyzed to determine the average number of re-uses before the dialyzer failed the 80% TCV (total cell volume) criteria set by the FDA. FIG. 2 is a graph of the number of re-uses prior to failure. The mean re-use number of Method A is about 5 and that of Method B was about 10. This means that using method A, 50% of the dialyzers failed after 5 re-uses, and using method B, 50% of the dialyzers failed after 10 re-uses. These average re-use numbers are very low for cost effective dialysis treatment.

It is believed that method A is inadequate in both the chemical composition of the cleaning solution and the fluid dynamics needed to achieve effective cleaning. Method B is deficient because of the acid pH of peracetic acid, and the lack of fluid dynamics needed to overcome the adhesion of blood clots and protein deposits from the hollow fibers and the regions under the cap of the dialyzer. The decrease in water permeability shown in method B, and its poor pore structure cleaning, decreases the removal of middle solutes such as beta-2M.

Control 2

Five dialyzers were cleaned with Renalin® at pH 3.0 from the dialysate side for 7 minutes by backflushing at 450 ml/min, but the average TCV was only 71 ml. Thus the use of an acid solution of Renalin® does not recover the TCV of failed dialyzers.

Control 3

The method of Control 1, Method B, was repeated except supplying filtered air through the lumen side for 7 minutes at the same time as they were cleaned with Renalin®. The average TCV was 71 ml. Thus no improvement was noted for this acidic solution even when using two phase flow.

Control 4

The method of Control 3 was repeated except using as the cleaning solution sodium chloride having a pH of 7.0 passed to the dialyzate side and filtered air passed through the lumen side for 7 minutes. No improvement in TCV was obtained. Thus two phase flow and a neutral pH did not clean the dialyzers so they could be re-used.

EXAMPLE 1

Eight dialyzers (F80A) made by the Fresenius Co. of Bad Homburg, Germany, were cleaned using a method of the invention. The internal diameter of a hollow fiber was 0.2 mm and the length to diameter ratio of each fiber was 1100. A bundle of 15,000 parallel, hollow fibers made of polysulfone, or a derivative thereof, was used. A cleaning agent of 0.225% sodium hypochlorite (NaOCl) and 200 ppm Cremophor EL nonionic surfactant, a castor oil ethoxylate, having a pH of 11.3, was passed into the dialysate side of the dialyzers and mixed with air delivered from the blood/lumen side of the dialyzers to form a mixed phase flow mixture in situ inside the hollow fibers. Cleaning was carried on for 7 minutes, following by rinsing with water, filling with Renalin® and storing for at least 13 hours prior to re-use. The dialyzer was cleaned and reprocessed after each dialysis session.

This cleaning method was continued for 22 re-uses. The TCV was measured after each reprocessing to ensure the dialyzer passed the 80% TCV criterion. None of these eight dialyzers failed this criterion through 22 re-uses. The fibers had excellent color, the under the cap regions were clean, and no fiber leaks occurred.

Figure 3:
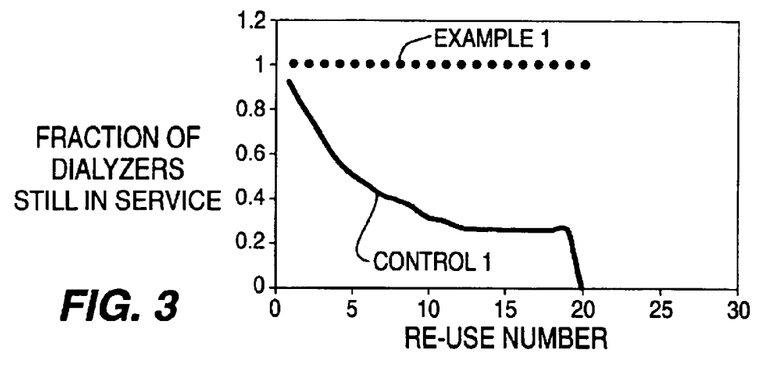
FIG. 3 is a graph comparing the number of re-uses for dialyzers cleaned according to a prior art method with the method of the invention.

FIG. 3 compares the results of Control 1 and this Example. A complete recovery of TCV was obtained for at least 22 re-uses for dialyzers treated as above, whereas the conventional method A does not.

EXAMPLE 2

The method of Example 1 was repeated using a cleaning solution of sodium hydroxide (pH 12.6) for 7 minutes on a re-used dialyzer which had a TCV of only 66 ml, except that the solution he was pumped into the dialysate side for 2 minutes and air added from the other side. The alternate side sequence was continued for 5 minutes.

The calculated Reynolds number of flow in the hollow fibers was about 200, based on the known flow rate and the cross-sectional area of air flow, the fiber diameter and the air viscosity.

The hemodialyzer was rinsed with water. The TCV was 105 ml, an improvement of 59%. It is believed this improvement was due to the efficient removal of proteins, blood cells and components from the lumens. There was no visible blood or hard protein deposits in the header under the cap regions.

After rinsing, Renalin® was added as a disinfectant.

An additional 16 dialyzers were processed as above. The average improvement was 21.1±13.6 ml, or an improvement of 31%.

Water permeability of the cleaned dialyzers was also measured and found to improve by 325±39, an indication that the pore structure was improved about 80–100% based on nominal values. This improvement in water permeability is an indication that dialyzers cleaned with the method and cleaning composition of this invention would have an improved removal of middle solute molecules, such as beta-2M.

EXAMPLE 3

The method of Example 2 was repeated on a failed hemodialyzer sterilized with Renalin® using as the cleaning solution 0.225% of NaOCl and 200 ppm of a surfactant, Cremophor EL, having a pH of 11.3, for a total cycle of 7 minutes.

The TCV was 104 ml, an improvement of 45 ml, or 76% increase in TCV.

Eighteen additional failed hemodialyzers were processed as above. A 29% improvement was obtained, 90% of these failed dialyzers were now usable, with a TCV above the 80% level as required by the FDA.

EXAMPLE 4

A hemodialyzer was cleaned by the two phase flow method of Control 3 using NaOH for a total cycle of 7 minutes. The TCV was only 56 ml, inadequate for re-use.

The hemodialyzer was then cleaned using the method of Example 2 and a cleaning solution of sodium hydroxide, NaOH, having a pH of 12.8. No traces of blood or deposits could be seen. The dialyzer was rinsed with water for 10 minutes when the TCV was measured to be 99 ml, an improvement of 43 ml or 77% increase in TCV.

Five additional failed hemodialyzers were processed as above. The TCV improvement was 28.5±8.0 ml, an increase of 44%. The average improvement in water permeability of 352±16 ml corresponds to an increase of 123%. Thus use of a solution having a pH of 12.8 is better than one having a pH of 12.6, as used in Example 2.

EXAMPLE 5

The method of Example 2 was repeated except using as the cleaning solution NaOH, at a pH of 12.6, and having a temperature of 40° C.

After cleaning, the dialyzer was rinsed with water and had a TCV of 101 ml, an improvement of 32 ml or 46%. Visual observation of the fibers showed no blood residues or deposits.

The improvement in water permeability was 255 ml, corresponding to an increase of 98%.

EXAMPLE 6

Five used hemodialyzers having an average TCV of 73.8 ml were cleaned in accordance with the method of Example 2 with a cleaning solution of 0.5% sodium gluconate, a chelating or sequestering agent effective at an alkaline pH, 0.25% of hydrogen At peroxide and sodium hydroxide added to bring the pH to 11.3.

After rinsing with water for 10 minutes, the TCV was improved by an average of 22.2±5 ml, corresponding to a 30% increase.

EXAMPLE 7

A group of six failed dialyzers, having an average TCV of 76±4.7 ml, were cleaned according to the method as above, except that 0.2% of a nonionic alkyl glucoside surfactant NPS, available from the Burlington Company, was added. The pH of the cleaning solution was adjusted to 11.3.

The average improvement in TCV was 18.3±11.6 ml, an increase of 24%. Thus a cleaning solution of an alkalizing agent, a chelating and sequestering agent, a nonionic surfactant and hydrogen peroxide improved the cleaning.

EXAMPLE 8

The cleaning method of Example 7 was repeated except 0.1% of an anionic surfactant, sodium dodecyl sulfate (SDS) was added instead of the nonionic surfactant. The improvement in TCV was 6 ml. Thus an anionic surfactant can also be used with two-phase flow to clean dialyzers under high pH conditions.

EXAMPLE 9

A group of 11 used hemodialyzers were reprocessed using Renalin®. The average TCV was only 82.2±8.0 ml.

These dialyzers were then cleaned using the present two-phase flow procedure with a cleaning solution of 1.2% of sodium gluconate, 0.25% of hydrogen peroxide and 0.2% of sodium phosphate tripoly (SPT). The pH was raised to 11.3 using sodium hydroxide.

After rinsing with water for 10 minutes, the TCV was increased an average of 20.0±10.9 ml, a 24% increase.

EXAMPLE 10

The cleaning method of Example 9 was repeated except adding 0.02% of a nonionic alkyl glucoside surfactant 816 available from the Burlington Company, and omitting the hydrogen peroxide.

After rinsing with water, the TCV was improved by 20 ml, an increase of 24%. Thus hydrogen peroxide can be omitted and a combination of a glucoside surfactant, and a sequestering agent at a high pH can also be used.

EXAMPLE 11

The cleaning method of Example 10 was repeated on five failed dialyzers having an average TCV of 83±6.5 ml, except adding 1% of hydrogen peroxide. The average improvement in TCV was 15.8±8.1 ml, or an increase of 19%. The dialyzers had excellent whitening and good appearance.

EXAMPLE 12

The cleaning method of Example 10 was repeated on three failed dialyzers having an average TCV of 82.3±9.9 ml except using as the cleaning solution 0.6% of SPT, 0.25% of hydrogen peroxide and 0.05% of nonionic NPS surfactant. The pH was 11.3. The average improvement in TCV was 15.7±10.1 ml, or an increase of 19%.

EXAMPLE 13

A group of five used hemodialyzers was cleaned in accordance with the procedure of Example 6 using a mixture of 0.3% of sodium gluconate, 0.3% of SPT, and 0.3% of sodium carbonate, and raising the pH to 11.3 using sodium hydroxide. The initial average TCV was 76.4±6.2 ml. After cleaning and rinsing, the average improvement in TCV was 18.0±4.9 ml, a 23% increase. Thus sodium carbonate can be used with an alkaline cleaning agent.

EXAMPLE 14

A group of five dialyzers having an average TCV of 74.2±6.2 ml was cleaned according to the method of Example 13 except adding 0.02% of a nonionic surfactant alkyl glucoside 816 of the Burlington Company.

The average increase in TCV was 19.4±7.1 ml, an increase of 26%.

EXAMPLE 15

A group of two used dialyzers having an average TCV of 78±5.6 ml was cleaned using a cleaning solution of 0.66% of SPT only, raising the pH to 11.3 using sodium hydroxide. The average improvement was 24.5±0.7 ml, or an improvement of 31%. Thus a sequestering or chelating agent alone, in a high pH solution, can be used to clean dialyzers and restore their function.

EXAMPLE 16

A dialyzer was cleaned in accordance with the method of Example 6 except using as the cleaning solution 1% sodium phosphate tripoly, or SPT, and 1% sodium carbonate. The pH was raised to 11.5 with sodium hydroxide. A 25 ml improvement in TCV was obtained. Thus a cleaning solution of a sequestering or chelating agent and sodium carbonate at a high pH can be used to clean and restore dialyzers with the present two-phase flow method.

EXAMPLE 17

A group of two Fresenius Optiflux 200A used polysulfone-based dialyzers having an average TCV of 79 ml was cleaned using a cleaning solution of 0.5% sodium gluconate, 0.5% SPT and 0.25% hydrogen peroxide. The pH was increased to 11.9 using sodium hydroxide. The average improvement in TCV was 17.5 ml, or an improvement of 22%.

EXAMPLE 18

A group of two used Polyflux 17R™ dialyzers made by Gambro Renal Products of Lakewood, Colo., made of polyamide fibers and having an average TCV of 85 ml, was cleaned using the cleaning solution of Example 17. The average improvement in TCV was 22.5 ml, an improvement of 26%.

EXAMPLE 19

A used cellulose acetate dialyzer, Clirans® T220, made by the Terumo Medical Corporation of Tokyo, Japan, having a TCV of 85 ml, was cleaned using the cleaning solution of Example 17. The improvement in TCV was 49 ml, or an improvement of 57%.

EXAMPLE 20

A group of six used dialyzers was cleaned in accordance with the invention, except first passing a 0.05% heparin-0.9% saline solution as a two phase flow mixture at a flow rate of 70 ml/min Oft and an liquid to air ratio of 1:1300, through the dialyzers via the blood side. A cleaning solution as in Example 2 was then used from the dialysate side in accordance with the invention. The pH was 12.6.

The average TCV improvement was 31.0±14.2 ml, an improvement of 52%. The improvement in water permeability was 302±46, an improvement of 111%.

Thus two compositions can be used to clean dialyzers; one from the lumen side to unclot blood and to remove residues from hollow fiber lumens and from under the cap regions, without affecting the pore size distribution of the membrane layer. The second (cleaning) composition can be applied, either sequentially or simultaneously, from the dialysate side, mixing it with air, to clean the pore structure and assist in overall cleaning. This method eliminates the addition of bleach which is related to albumin loss in the patient when used from the dialysate side.

EXAMPLE 21

A group of six used hemodialyzers that had been cleaned using a Renatron® machine and sterilized with Renalin® were cleaned in accordance with the invention using a solution of 0.225% sodium hypochlorite (NaOCl) in 1% sodium bicarbonate solution. The pH was 8.6. After rinsing with water, the TCV improved by an average of 29.3±5.2 ml, corresponding to an increase of 44%. Thus cleaning was effective even at a low pH.

The cleaning was repeated for another set of two dialyzers with the cleaning solution at room temperature. The average improvement in TCV was 32.5±2.1 ml, corresponding to an increase of 52%.

The cleaning was repeated for another dialyzer, except that the cleaning solution included 0.4% of NaOCl and cleaning was carried out at room temperature. The pH was still 8.6. The TCV improved by 29 ml, corresponding to an increase of 45%.

Cleaning was repeated for a set of three dialyzers except that the cleaning solution contained 0.75% of NaOCl and was not heated. The pH of the solution was 8.8. The average improvement in TCV for three samples was 19.3±15.0 ml, corresponding to an increase of 27%.

Cleaning was repeated for a set of four dialyzers except that the cleaning solution contained 0.1% of NaOCl and was not heated. The pH was 8.4. The average improvement for four samples in TCV was 19.2±4.7 ml, corresponding to an increase of 28% in TCV.

EXAMPLE 22

In this Example, eight used dialyzers were first cleaned without two phase flow. Cleaning was then repeated using the two phase flow of the invention. The cleaning solution was NaOH having a pH of 12.6.

The average TCV after the first cleaning was 89±8.8 ml, an improvement of 29%. The improvement in water permeability was 292±32 ml, an increase of 102%. However, three of the dialyzers did not satisfy the 80% TCV criteria required by the FDA.

Thus the dialyzers were re-processed using the method of the invention. The TCV further improved by 8.0±7.8 ml and permeability improved by 41±28 ml. All of the dialyzers now satisfied the 80% TCV criteria and became re-usable for dialysis treatment.

Although at high pH cleaning by backflushing can recover TCV and water permeability values, the two phase flow of the invention is needed to achieve full recovery of the dialyzer functions including TCV and water permeability, and also including solute clearance, under the cap cleaning and uniform cleaning of both the arterial and venous sides of the dialyzer. The composition of the cleaning solution also constitutes a critical portion of the present invention.

EXAMPLE 23

This example used dialyzers fouled by operating in the ultrafiltration mode using a Bovine Serum Albumin (BSA) solution for several hours. The water permeability was 645 ml/min at 10 psig.

The dialyzers were cleaned with 1% phosphoric acid at 1100 ml/min and room temperature and air at 52 psig for 5 minutes from the dialysate side. The permeability was 650 ml/min, only a 1% recovery.

The same dialyzer was cleaned again using NaOH solution at pH 12.6 at 60° C. and air at 51 psig for 5 minutes using a flow rate of 1000–1100 ml/min. The water permeability improved to 855 ml, a 31.5% improvement.

A second fouled dialyzer having a water permeability of 535 ml/min was cleaned with NaOH solution at pH 11.9 at 46° C. and air at 52 psig for five minutes from the diasylate side. The permeability was 720 ml/min, an improvement of 34%.

A third fouled dialyzer using 0.6% BSA and 0.9% NaCl had a water permeability of 430 ml/min. It was cleaned with NaOH having a pH of 11.0 at 10 psig, when the permeability was 430 ml/min. Thus no improvement was shown. It was cleaned again using NaOH at a pH of 11.9 and 52 psig of air at a flow rate of cleaning solution of 1000 ml/min. The permeability improved to 515 ml/min, an improvement of about 20%.

EXAMPLE 24

A series of experiments with Fresenius F80A dialyzers that failed the 80% TCV criterion were cleaned according to the method of Example 1, but using cleaning solutions having varying pH. Increasing the pH increased the TCV recovery. At a pH of 7 and higher, improvement becomes considerable. At a pH of 11.3, improved results are obtained when 0.225% of bleach is added.

Figure 4:
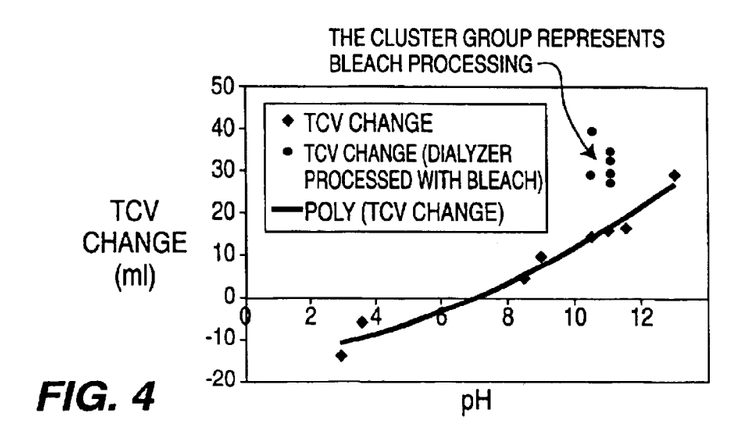
FIG. 4 is a graph showing the effect of pH on TCV change of used dialyzers processed by the two phase flow method of the invention.

The above results were compared to a series of experiments using Renalin®, which has a pH of 3–4. No improvement in TCV was obtained with the latter. The results are summarized in FIG. 4.

EXAMPLE 25

Eight dialysis patients received dialysis using Fresenius F80A dialyzers which were cleaned using the method of Example 1, while 7 Control patients received dialysis using dialyzers processed with Renatron® using Renalin®.

Urea clearance using the method of this invention was 7% higher than the Control group. Beta-2M reduction ratio (measured as the post-dialysis beta-2M concentration in mg/l divided by pre-dialysis concentration) was significantly higher—by a factor of 2 (57.5% using the method of the invention versus 27.1% for the Control group). These results are comparable to that obtained when using a new dialyzer. Further, the concentration of beta-2M in patients decreased to 11.3 mg/l after the third week of dialysis treatment, whereas the concentration for the Control group patients was 36.7 mg/l. Albumin loss for the two groups was within the acceptable level as defined by dialyzer manufacturers.

The removal of middle solute beta-2M by as much as 50% improves the dialysis results in patients as well.

The following Examples are directed to water treatment using the two phase cleaning method of the invention.

EXAMPLE 26

A five meter long flexible polyvinylchloride (PVC) tubing with a diameter of 1.2 mm and l/d 4200, was connected to a municipal water supply system and the water allowed to flow intermittently for 10 seconds every 10 minutes for a period of over six months. The biofilm grown under these condition was quantified to have $2 \times 10^6 CFU/cm^2$ before it was cleaned. The tubing was cut into two equal lengths and cleaned for five minutes according to method 3 of this invention (liquid to gas ratio was 1:920) using two liquid compositions, one at pH 3.0 and the other at pH 11.0. The acid liquid cleaning solution was based on citric acid including 0.1% of a nonionic surfactant Tergitol-1X made by Union Carbide Company. The alkaline liquid cleaning solution was based on sodium hydroxide including 0.1% of Tergitol-1X. The results showed that the alkaline liquid cleaning solution applied according to method 3 achieved complete removal of the biofilm (0 $CFU/cm^2$) from the tubing, whereas the acid composition only removed about one-half of the original biofilm

EXAMPLE 27

A 1.4 mm diameter tubing having a length of 24 inches (l/d 435) was covered with a highly adherent biofilm on its interior surface and cut in three equal sections, A, B and C. Section A was used as a Control. It was cleaned by scaping the biofilm with a scalpel and found to contain a total of $2.5 \times 10^8$ CFU.

Section B was cleaned in a slug flow regime by mixing air and a cleaning solution at a liquid to air ratio of 1:1 to 1:10, including 0.15% Tergitol-1X, 1% of SPT and 0.18% of sodium silicate for ten minutes, with an inlet air pressure of 60 psig. A total of $2.5 \times 10^8$ CFU was found, indicating that this method was not effective in removing biofilm.

Section C was cleaned with the same cleaning solution with two phase flow according to method 3 of this invention, where a two phase flow mixture with a liquid to gas ratio of 1:920 was applied for 10 minutes at 60 psig air pressure. A total of 800 CFU was found, indicating that the present method is effective in removing highly adherent biofilm.

EXAMPLE 28

An ultrafiltration hollow fiber membrane module, Polymem 0.85 mm of the Polymem Corporation, used in water treatment (l/d of each hollow fiber was about 2000) was fouled for two weeks using surface water containing synthetic humic acid until the flux decreased to about 60% of its original value. The module was then cleaned using a cleaning solution of 0.01N NaOH and 0.1% of SDS surfactant according to the method of the invention. The liquid to gas ratio was 1:550 at 25 psig pressure drop. After using two phase flow cleaning for 90 seconds, the flux of the module recovered to 100%.

EXAMPLE 29

A Polymem 1.4 mm ultrafiltration hollow fiber membrane module made by the Polymem Corporation of France wherein the hollow fibers had a l/d of about 1500 was treated as in Example 26. After cleaning for 120 seconds, the flux of the module was recovered to 100%.

The following Example was used to clean a piping system used to carry foodstuffs made of milk.

EXAMPLE 30

A stainless steel piping system having a l/d of about 3000 and having an internal diameter of 2 inches was fouled by passing raw milk through the pipe for four hours. Test sections were placed at 50 foot intervals along the pipe. A premixed two phase flow having a liquid to air ratio of 1:500 to about 1:2500, an inlet air pressure of 12–32 psig was used to clean the pipe. Estimated air velocities at the beginning and end of the piping system were about 63–86 ft/sec and about 115–272 ft/sec respectively. The pipe was then cleaned, rinsed and sanitized according to the method of Example 28.

The cleaning was repeated using an acid cleaning agent for two minutes to remove milk calcium deposits. Cleaning was evaluated by visual inspection of the test sections, by weighting test sections before and after cleaning, and by microscopic examination.

The present method was superior and consumed only about 2% of the cleaning liquid in a fraction of the time required by the liquid only circulation method.

The pipes were then rinsed with water and air for ten minutes. The piping system was then sanitized for eight minutes with peracetic acid in conventional manner. The disinfection was equivalent. However, the present method saved about 95% of the sanitizing solution.

EXAMPLE 31

A flow of water was maintained through a ⅜ inch internal diameter plastic tubing having a l/d of about 1800 for three months to simulate soda fountain conditions in the field. A thick biofilm formed on the tubing. The tubing was cleaned according to the method of Example 28 using an alkaline cleaning agent including 0.1% of Tergitol-1X surfactant at a pH of 11.5 for five minutes. The liquid to air ratio was 1:1800 and the pressure was 45 psig. Air velocities at the inlet and the outlet of the tube was 50 ft/sec and 250 ft/sec respectively. Complete removal of the biofilm from the entire length of the tubing was obtained as measured by standard microbiology methods. Thus the shear stress of the two phase flow was high enough to overcome the biofilm adhesion having an adhesive strength in excess of 100 Pascals.

Thus the two phase flow method of the present invention is applicable to cleaning passageways having a high length/diameter (l/d) ratio. When the fiber diameter is very small, as is the case with dialyzers, a diameter of only 150–200 microns has an l/d of about 1100. Long piping systems having diameters in the range of ⅜ to 4 inches or more, have a high l/d. Dairy and beverage lines and water systems can be as long as 300–600 feet, or even longer, with an l/d of up to about 3000 or more.

Cleaning high l/d lines with conventional liquid flushing uses large amounts of liquid chemicals solutions that cannot always be discharged directly to the environment. The two phase method of the invention effectively cleans, rinses and sanitizes such lines using only small amounts, i.e., less than 5%, of cleaning agents and rinse water. Further, the time required for cleaning is substantially shortened. As long as sufficient air can be supplied so as to sustain an annular mist regime for the liquid—air mixture, one can clean piping systems having a high l/d. Liquid droplets sizes effecting localized cleaning in this dispersed two phase flow have a range between 20 microns to over 1 mm, depending on flow conditions.

Although the invention has been described by means of specific embodiments, it is not meant to be limited to the details therein. The invention is only meant to be limited by the scope of the appended claims.

We claim:

1. A method of removing contaminants from pores, lumens and under-the-cap regions of a hemodialyzer including a hollow fiber membrane bundle comprising
   backflushing the hollow fiber membrane bundle with a cleaning solution by pressurizing the cleaning solution from the dialysate side of the dialyzer,
   passing a gas under pressure into the lumen side of the dialyzer so as to form a two phase flow mixture with the backflushed cleaning solution that produces droplets that create shear or impact stresses on the lumen walls of the hollow fibers, and wherein said two phase flow mixture creates turbulence inside the under-the-cap regions of the hemodialyzer, thereby loosening and removing said contaminants from the dialyzer.

2. A method according to claim 1 wherein the cleaned dialyzer is rinsed with deionized water and filled with a liquid sterilant.

3. A method according to claim 1 wherein said cleaning solution includes an agent that unclogs the pores and lumens of the hollow fiber membranes.

4. A method according to claim 1 wherein said cleaning solution includes a chelating agent.

5. A method according to claim 1 wherein said cleaning solution is included with sodium hydroxide.

6. A method according to claim 1 wherein said cleaning solution has a temperature in the range of 20 to 60 degrees Centigrade.

7. A method according to claim 1 wherein said cleaning solution includes a surfactant.

8. A method according to claim 1 wherein said cleaning solution has a pH of at least 7.0.

9. A method according to claim 1 wherein said cleaning solution includes an oxidizing agent selected from the group consisting of a peroxy compound having an acidic pH.

10. A method according to claim 1 wherein said cleaning solution includes an oxidizing agent selected from the group consisting of a hypochlorite compound.

11. A method according to claim 1 wherein the direction of the two phase flow is periodically reversed.

12. A method according to claim 1 wherein the two phase flow is pulsed by stopping the flow of gas periodically while backflushing continues.

13. A method according to claim 1 wherein a pre-mixed liquid-gas two phase flow mixture is applied to the lumen side of the dialyzer prior to commencing the backflushing step.

14. A method according to claim 1 wherein the two phase flow cleaning is preceded by backflushing with a cleaning solution alone.

15. A method of removing contaminants from pores, lumens and under the cap regions of a hemodialyzer including hollow fibers comprising
    pressurizing a cleaning solution from the dialysate side of the hemodialyzer,
    passing a premixed mixture of a liquid and a gas into the lumen side of the hemodialyzer,
    combining said cleaning solution and said liquid-gas mixture so as to generate droplets that create shear or impact stresses that sweep the interior walls of the hemodialyzer fibers to remove the contaminant.

16. A method according to claim 15 wherein the cleaned dialyzer is rinsed with deionized water and filled with a liquid sterilant.

17. A method according to claim 15 wherein the cleaning solution and the liquid used to form the liquid-gas mixture are the same.

18. A method according to claim 15 wherein the cleaning solution and the liquid used to form the liquid-gas mixture are different.

19. A method according to claim 15 wherein the liquid useful to form the liquid-gas mixture includes an agent that unclogs the lumens of the hollow fibers of the hemodialyzer.

20. A method according to claim 19 wherein said agent is selected from the group consisting of heparin and a citrate solution.

21. A method according to claim 15 wherein said cleaning solution includes a chelating agent.

22. A method according to claim 15 wherein said cleaning solution includes a surfactant.

23. A method according to claim 15 wherein said cleaning solution has a pH of at least 7.0.

24. A method according to claim 15 wherein said cleaning solution includes a peroxy compound oxidizing agent, said solution having an acid pH.

25. A method according to claim 15 wherein said cleaning solution includes a hypochlorite compound oxidizing agent.

26. A method according to claim 15 wherein said cleaning solution includes sodium hydroxide.

27. A method according to claim 15 wherein said cleaning solution has a temperature of from 20 to 60 degrees Centigrade.

28. A method according to claim 15 wherein the direction of the liquid-gas mixture is periodically reversed.

29. A method according to claim 15 wherein the liquid-gas mixture cleaning is preceded with a backflushing the lumen side using a cleaning solution alone.

30. A method according to claim 15 wherein the liquid-gas mixture cleaning is followed by backflushing the lumen side using a cleaning solution alone.

31. A method of removing contaminants from lumen and under-the-cap regions of a hemodialyzer including hollow fibers comprising
    passing a pre-mixed mixture of a cleaning solution and a gas into the lumen side of the hemodialyzer so as to generate droplets that create shear or impact stresses on the lumen walls of the hollow fibers, and wherein said mixture creates turbulence inside the under the cap regions of the hemodialyzer, thereby loosening and removing said contaminants from the hemodialyzer.

32. A method according to claim 31 wherein the cleaned hemodialyzer is rinsed with deionized water.

33. A method according to claim 31 wherein said cleaning solution includes a chelating agent.

34. A method according to claim 31 wherein said cleaning solution includes a surfactant.

35. A method according to claim 31 wherein said cleaning solution has a pH of at least 7.0.

36. A method according to claim 31 wherein said cleaning solution includes a hypochlorite compound oxidizing agent.

37. A method according to claim 31 wherein said cleaning solution includes sodium hydroxide.

38. A method according to claim 31 wherein the temperature of said cleaning solution is in the range of 20 to 60 degrees Centigrade.

39. A method according to claim 31 wherein the direction of the two-phase flow is periodically reversed.

40. A method according to claim 31 wherein the two-phase flow cleaning is preceded by backflushing using a cleaning liquid alone.

41. A method according to claim 31 wherein the two-phase flow cleaning is followed by a backflushing using a cleaning liquid alone.

42. A method for cleaning a hemodialyzer having a housing a bundle of hollow permeable membrane fibers within the housing, a dialysate side inlet and outlet, and a lumen side inlet and outlet, the method comprising steps of:
   (a) pressurizing a liquid cleaning solution in the dialysate side to infiltrate the liquid cleaning solution into the lumen side, and
   (b) passing a gas into the lumen side to form a mixture of the gas and the liquid cleaning solution in the lumen side.

43. A method according to claim 42, wherein the hollow permeable membrane fibers comprise ultrafiltration membranes.

44. A method according to claim 42, wherein the hollow permeable membrane fibers comprise nanofiltration membranes.

45. A method according to claim 42, wherein the hollow permeable membrane fibers comprise reverse osmosis membranes.

46. A method according to claim 42, wherein the gas is applied to the lumen side at a velocity of 10 ft/sec to 500 ft/sec.

47. A method according to claim 42, wherein droplets are formed within the lumen side.

48. A method according to claim 47, wherein the droplets have a diameter of about 20 microns and higher.

49. A method according to claim 47, wherein the droplets have a diameter of 50 microns to 250 microns.

50. A method according to claim 42, wherein the liquid cleaning solution to gas ratio in the lumen side is between 1:50 and 1:6,000.

51. A method according to claim 42, wherein the cleaned hemodialyzer is rinsed with deionized water and filled with a liquid sterilant.

52. A method according to claim 42, wherein said liquid cleaning solution includes a chelating agent.

53. A method according to claim 42, wherein the liquid cleaning solution is made with sodium hydroxide.

54. A method according to claim 42, wherein the liquid cleaning solution has a temperature in the range of 20° C. to 60° C.

55. A method according to claim 42, wherein the liquid cleaning solution includes a surfactant.

56. A method according to claim 42, wherein the liquid cleaning solution has a pH of at least 7.0.

57. A method according to claim 42, wherein the liquid cleaning solution includes a peroxy compound having an acidic pH.

58. A method according to claim 42, wherein the liquid cleaning solution includes a hypochlorite.

59. A method according to claim 42, wherein the two phase flow is pulsed.

60. A method according to claim 42, comprising applying a pre-mixed liquid-gas two phase flow mixture to the lumen side.

61. A method for cleaning a hemodialyzer having a housing a bundle of hollow permeable membrane fibers within the housing, a dialysate side inlet and outlet, and a lumen side inlet and outlet, the method comprising:
   (a) passing a mixture of a liquid and gas into the lumen side of the hemodialyzer.

62. A method according to claim 61, further comprising pressurizing a cleaning solution in the dialysate side of the hemodialyzer.

63. A method according to claim 62, wherein the cleaning solution and the liquid used to form the liquid-gas mixture are the same.

64. A method according to claim 62, wherein the cleaning solution and the liquid used to form the gas-liquid mixture are different.

65. A method according to claim 61, wherein the hollow permeable membrane fibers comprise ultrafiltration membranes.

66. A method according to claim 61, wherein the gas is applied to the lumen side at a velocity of 10 ft/sec to 500 ft/sec.

67. A method according to claim 61 wherein droplets are formed within the lumen side.

68. A method according to claim 67, wherein the droplets have a diameter of about 20 microns and higher.

69. A method according to claim 67, wherein the droplets have a diameter of 50 microns to 250 microns.

* * * * *